(12) United States Patent
Bevot et al.

(10) Patent No.: US 8,286,470 B2
(45) Date of Patent: Oct. 16, 2012

(54) METHOD FOR OPERATING A HEATABLE EXHAUST GAS PROBE

(75) Inventors: Claudius Bevot, Stuttgart (DE);
Eberhard Schnaibel, Hemmingen (DE);
Jens Wagner, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 448 days.

(21) Appl. No.: 12/564,228

(22) Filed: Sep. 22, 2009

(65) Prior Publication Data

US 2010/0073017 A1  Mar. 25, 2010

(30) Foreign Application Priority Data

Sep. 22, 2008  (DE) .......................... 10 2008 042 268

(51) Int. Cl.
*G01M 15/10* (2006.01)
(52) U.S. Cl. ................................................ 73/114.69
(58) Field of Classification Search ............... 73/114.69, 73/114.71, 114.73, 114.72
See application file for complete search history.

(56) References Cited

U.S. PATENT DOCUMENTS

| | | | |
|---|---|---|---|
| 6,763,697 B2 * | 7/2004 | Bolz | 73/23.2 |
| 6,861,850 B2 * | 3/2005 | Bolz | 324/691 |
| 6,898,928 B2 * | 5/2005 | Wagner et al. | 60/285 |
| 7,017,567 B2 * | 3/2006 | Hosoya et al. | 123/697 |
| 2002/0008100 A1 * | 1/2002 | Hosoya et al. | 219/494 |
| 2003/0074889 A1 * | 4/2003 | Wagner et al. | 60/284 |
| 2004/0011029 A1 * | 1/2004 | Wagner et al. | 60/295 |
| 2004/0173196 A1 * | 9/2004 | Hosoya et al. | 123/697 |
| 2009/0308135 A1 * | 12/2009 | Reinshagen et al. | 73/23.2 |

* cited by examiner

*Primary Examiner* — Eric S McCall
(74) *Attorney, Agent, or Firm* — Merchant & Gould P.C

(57) ABSTRACT

A method for operating an exhaust gas probe, in particular a lambda probe, in the exhaust gas of an internal combustion engine, where at least one heating element for achieving the operating temperature in the exhaust gas probe and determination of the temperature of the exhaust gas probe is performed by measuring the internal resistance. Measurement of the internal resistance occurs by the superimposition of discrete bipolar test pulses that include a pulse and a counter pulse, and by acquisition of the Nernst voltage.

14 Claims, 3 Drawing Sheets

METHOD FOR OPERATING A HEATABLE EXHAUST GAS PROBE

This application claims benefit of Serial No. 10 2008 042 268.1, filed 22 Sep. 2008 in Germany and which application is incorporated herein by reference. To the extent appropriate, a claim of priority is made to the above disclosed application.

TECHNICAL FIELD

The present invention relates to a method for operating an exhaust gas probe, wherein the temperature of the exhaust gas probe is determined by measuring the internal resistance $R_i$ of the exhaust gas probe.

BACKGROUND

Catalytic converters are employed today for the purification of exhaust gases. Certain relationships of the components in the exhaust gas are required for an optimal functioning of the catalytic converters. In order to be able to appropriately set these relationships, exhaust gas probes are employed, which are provided for measuring the concentration of a certain component in the exhaust gas. In particular oxygen probes, so-called lambda probes, are employed for this purpose.

Oxygen probes basically have an ionic conductive, solid electrolyte lying between two electrodes. Both electrodes can be impressed with a measuring voltage. Depending on the oxygen content and the gas to be measured, a limit current, respectively a Nernst voltage, arises which is a function of the difference of the oxygen concentrations at the electrodes.

In order to achieve the necessary ionic conductivity of the solid electrolyte, a certain operating temperature of the exhaust gas probe is required. Moreover, the measuring accuracy depends on the temperature of the probe. For this reason, it is generally required to heat the probe and to control the temperature and if need be to control said temperature in a closed loop. A separate thermocouple for measuring the temperature can be eliminated as a rule. The highly temperature-dependent internal resistance $R_i$ of the exhaust gas probe can be accessed in order to obtain a measuring signal for the sensor temperature.

In the case of a pure 2-point lambda probe, a pulsed $R_i$ measurement is conventionally used. In so doing, in a low-frequency range, for example smaller than 1 Hz, a current pulse of 0.5 mA to 1 mA is applied for the duration of 1-10 ms as a load to the probe for diagnostic purposes. Approximately 1 ms after switching on the current, the increase in voltage is measured. The internal resistance value measured in this way is sufficiently stable and accurate to allow for an assertion about the temperature of the probe. This method has, however, the disadvantage that a polarization of the probe is induced each time the probe is impressed with a current pulse for diagnostic purposes. This polarization has to first degrade before the probe is again available for a measurement of the Nernst voltage as an exhaust gas measurement. Particularly in the case of probes, which are aged or have cooled down, relatively long recovery phases are required for this purpose before the probe is again available for the exhaust gas measurement. This recovery phase can in particular require 20-30 ms.

In the case of continuous-action lambda probes, in particular in the case of broadband lambda probes, the Nernst voltage is constantly adjusted in a closed-loop. The controlled variable of this closed-loop control, the pump current, is the output signal of the exhaust gas probe and is used as the continuous measured value for the air ratio lambda. The temperature of the probe is also generally adjusted to a nominal value because the probe has to be operated in a narrow temperature range in order to guarantee the functionality and characteristics of the probe. A temperature measurement is required to adjust the temperature. As described at the beginning of the application, the highly temperature-dependent internal resistance $R_i$ of the probe is generally used for this purpose. Because in the case of a continuous-action lambda probe the temperature is to be adjusted very quickly and accurately around the nominal value, a temperature measurement with high frequency, particularly with a repetition rate of at least 10 Hz, has to be implemented. The use of a pulsed measuring method greatly limits the continuous measuring of the lambda probe because a closed-loop control of the Nernst voltage is not possible during the polarization of the probe accompanying the test pulses. No measured value can therefore be acquired for $O_2$.

In order to avoid this disadvantage, the internal resistance measurement of the probe is conventionally performed by impressing an alternating current on the Nernst cell while the voltage, which thereby arises, is accordingly evaluated. The required absence of a dc component is, for example, assured by a capacitive decoupling while the alternating current is impressed on the Nernst cell via a capacitor. In the case of probes with a pumped $O_2$ reference, the Nernst cell is additionally impressed with a direct current, which is produced via a discrete power source. The alternating current has its own frequency, for example 3 KHz, which lies outside of the frequency band, wherein the Nernst voltage is controlled in a closed loop. This alternating current signal can therefore be filtered out from the control variable, which is evaluated for the measurement of $O_2$, respectively for ascertaining the air ratio lambda. The filtering out of the disturbance induced by the applied alternating current, in particular this high frequency disturbance, is, however, only possible to a certain extent and requires a relatively high technical outlay. The German patent application publication DE 100 29 795 A1 describes, for example, a device for measuring the internal resistance of a linear lambda probe which has a voltage amplifier and a synchronous demodulator. The voltage amplification can be switched between two predefined values with the frequency of the AC voltage which is dropped across the internal resistance; and the output signal is flattened by means of a filter.

SUMMARY

The present invention in contrast takes up the task of providing a method, wherein the temperature of an exhaust gas probe can be determined by measuring the internal resistance $R_i$ of the exhaust gas probe during operation of said probe. Complicated solutions for measuring the temperature shall be avoided with the method, and at the same time as few as possible disturbing pulses are produced in the system in order to allow for a practically continuous measurement of $O_2$. The adjustment of the temperature by means of a sufficiently high frequency of the internal resistance measurement shall therefore be made possible without special, technical complexity; and in so doing, the disturbance of the output signal of the exhaust gas probe shall be held to a minimum.

In the case of the method according to the invention for operating an exhaust gas probe, in particular a lambda probe, the exhaust gas probe has at least one heating element for achieving the operating temperature of the exhaust gas probe. The determination of the temperature of the probe is performed by measuring the internal resistance $R_i$. This method is thereby characterized, in that the measurement of the internal resistance $R_i$ results from applying, respectively superimposing, discrete bipolar test pulses. The bipolar test pulses comprise in particular a pulse and a counter pulse. As a reaction to the test pulses, the Nernst voltage $U_N$ changes as a function of the temperature-dependent internal resistance $R_i$ and can be evaluated as a measurement for the temperature of the probe.

The method according to the invention almost completely avoids the disadvantages of conventional methods for pulsed internal resistance measurement. The application of current pulses for acquiring temperature-dependent voltage changes, i.e. for the internal resistance measurement, which is known from the technical field, causes a polarization of the probe, which has to initially be degraded in order that the use of the Nernst voltage as an input signal for the closed-loop control of the pump current in acquiring $O_2$ measured values can be continued. According to the invention, provision is in contrast made for each test pulse to be applied in the bipolar fashion, i.e. each pulse is followed by a counter pulse with the opposite sign. For example, a first positive pulse is followed by a negative pulse. In so doing, a polarization of the probe electrodes is largely avoided by the bipolar test pulse that was applied. The polarization, which in the technical field is induced by the applied diagnostic current and which disturbs the $O_2$ measurement, i.e. the adjustment of the pump current, is very small. The remaining error in measurement of the Nernst voltage is insignificant. The pulsed measuring method according to the invention for measuring internal resistance can be implemented with very little complexity in comparison to alternating currents for diagnostic purposes, so that it can be very advantageously employed.

The bipolar test pulses in the method according to the invention can consist of at least one positive pulse followed by at least one negative counter pulse. In other forms of embodiment, at least one negative pulse followed by at least one positive counter pulse can initially be applied.

In a preferred form of embodiment, the bipolar test pulses are very short, for example 0.1 ms to 5 ms. Bipolar test pulses, which are applied for a time duration of approximately 0.5 to 1 ms pro pulse, respectively counter pulse, are particularly preferred. On account of the shortness of the test pulses for diagnostic purposes, the influence on the Nernst voltage and thereby on the adjustment of the pump current for measuring $O_2$ is insignificantly small. The short test pulses are nevertheless sufficient for acquiring the voltage change as a measurement for the internal resistance $R_i$ of the probe. In contrast to the alternating currents for measuring the internal resistance, which are applied in the technical field, the discrete bipolar test pulses of the present invention have the advantage in that it is not required to filter out certain frequencies.

When the Nernst voltage is discretely scanned, the pulse durations of the bipolar test pulses can advantageously be applied in a magnitude corresponding to the evaluation times of the Nernst voltage. For example, in the case of an evaluation time of the Nernst voltage, in particular in the case of an analog to digital conversion (ADC), being 1 ms, the first pulse of the bipolar test pulse can be applied for a time duration of likewise approximately 1 ms and the counter pulse for 1 ms or less. In so doing, the disturbance superimposed on the Nernst voltage is so small, respectively insignificant, that a blocking out of the Nernst voltage for, for example, 1 ms to 2 ms does not affect the closed-loop control of the Nernst voltage at, for example, 450 mV.

In a particularly preferred configuration of the method according to the invention, the heating element of the exhaust gas probe is activated in a clocked manner, for example by a conventional pulse width modulation (PWM) of the output stage of the probe's heater. Furthermore, the bipolar test pulses are essentially synchronized with the clock frequency of the activation of the heating element. During a pulse width modulation (PWM), a technical variable alternates between two values and the duty cycle is modulated at a constant frequency. In so doing, the heating voltage can be controlled in such a way that dramatic fluctuations in the temperature are avoided, and the temperature is precisely adjusted. The required heater output, respectively heater voltage, is preferably calculated in a control unit and emitted to the heater via a corresponding pulse width modulation output stage. The temperature determined according to the invention, respectively corresponding values which characterize the temperature, preferably flows into the control system of the heating element. These values can, for example, flow into said control system via a digital closed-loop control algorithm.

The bipolar test pulses are advantageously applied during the switch-on and/or switch-off phase of the heating element, in particular during the switch-on and/or switch-off phase of the output stage of the heater. The test pulses preferably lie completely in the switch-on and/or switch-off phase of the heating element. By means of a synchronization of the repetition rate of the test pulses with the PWM clock frequency of the heating element, an application of the test pulses during the alternation between switching on and switching off the heating element, i.e. during the heater flank. During the heater flank, a crosstalk between the different current pulses can result, which would disturb the measuring of the internal resistance. Especially in this form of embodiment, a coupling of the heater with the current pulses, which are applied for measuring the internal resistance, does not therefore disturb the measuring of the internal resistance.

The synchronization with the clock frequency of the heating element is, for example, thereby implemented, in that when a predefined length of the switch-on time of the heating element, respectively the output stage of the heater, is exceeded, the bipolar test pulse for measuring the internal resistance is started when the heater is switched on. When the PWM clock frequency is, for example, 100 Hz, the predefined length of the switch-on time can, for example, be 2 ms. As soon as the switch-on time undershoots a certain predefined length, for example 3 ms, the bipolar test pulse is started when the output stage of the heater is switched off. As soon as the switch-on time exceeds a further certain predefined length, for example 7 ms, the bipolar test pulse is started again when the heater is switched on. Preferably only one test pulse per switch-on phase, respectively switch-off phase, occurs in each case. In a particularly advantageous manner, both thresholds are set as far away as possible from each other so that the status of the test pulse has to be changed relatively seldom. In another form of embodiment, the synchronization can thereby result, in that when a predefined length of the switch-on time or the switch-off time, for example 7 ms, is undershot, the bipolar test pulse, respectively test pulse sequence, is delayed by this respective length. This process can be implemented with less complexity, a synchronization being achieved in a comparable manner.

An additional advantage of the synchronization of the frequency of the discrete bipolar test pulses with the clock frequency of the heater is that the temperature measurement is adapted to the thermal inertia of the probe. As a rule, a frequency of the test pulses of approximately 100 Hz is sufficient to allow for a closed-loop control of the heating with sufficient dynamics. Higher or lower frequencies for the bipolar test pulses can be employed as a function of the thermal characteristics of the exhaust gas probe.

Provision is made according to the invention for the Nernst voltage to be acquired to ascertain the internal resistance $R_i$ as a measurement for the temperature as well as to be an input signal for the closed-loop control of the pump current of the lambda probe. In this instance, the Nernst voltage is advantageoulsy acquired via at least one sample and hold circuit, preferably via only one sample and hold circuit. Provision is made in a particularly advantageous fashion for the closed-loop control of the pump current of the lambda probe and/or the closed-loop control of the heating element to occur via a digital closed-loop control algorithm, the Nernst voltage acquired, for example, via a sample and hold circuit flowing as an input variable into the digital closed-loop control algorithm.

In a preferred configuration of the method according to the invention, the use of the Nernst voltage as the input signal for the closed-loop control of the pump current of the exhaust gas probe during the measurement of the internal resistance $R_i$, respectively during the application of the discrete bipolar test pulses, is suspended. Because the bipolar test pulses are only applied for relatively short time durations, the influence of the disturbance superimposed on the Nernst voltage is relatively small. The closed-loop control of the pump current is not significantly affected by a suspension, respectively blocking out, of the Nernst voltage for this time period. This suspension and a maintenance, respectively freezing, of the values is very simple to implement without complexity. The loss of control time lies thereby in the range of, for example, 5% to 10% and does not significantly influence the accuracy and reliability of the acquisition of the Nernst voltage, respectively the closed-loop control of the pump current for acquiring values for $O_2$.

Provision is made in a preferred configuration of the method according to the invention for theoretical measured values to be augmented for the acquisition of the Nernst voltage during the measurement of the internal resistance $R_i$, respectively during the time period, wherein the bipolar test pulses are applied, in that, for example, appropriate theoretical values, which compensate for the effect of the test pulses on the Nernst voltage, are inputted for the closed-loop control of the pump current so that a suspension of said closed-loop control and with it a suspension of the acquisition of measured values for $O_2$ during the application of the bipolar test pulses and the reaction of the system does not occur. The influence of the bipolar test pulses on the Nernst voltage, respectively the closed-loop control of the pump current, can be mathematically compensated. A mathematical compensation with regard to the Nernst voltage, which is influenced by the superimposed test pulses, is thereby particularly possible, in that the value for the internal resistance changes only very slowly due to the thermal inertia of the probe's ceramic insulation. For this reason it can be assumed that the value of the internal resistance with respect to a value from an earlier measurement changes only marginally. The measured value from the earlier measurement for the internal resistance can therefore be used as an approximation for the mathematical compensation of the effect of the test pulses during the closed-loop control of the pump current. In the case of constantly changing values for the internal resistance, said measured value can analogously be taken into account during the mathematical compensation, in that progressions of the internal resistance are taken as a basis for the mathematical compensation. A mathematical compensation can especially be implemented when a digital processing is used. In so doing, the particular advantage lies in the fact that the loss of control time for the Nernst voltage caused by the bipolar test pulses can be blocked out. The inaccuracies resulting from the theoretical values, respectively the mathematical compensation, are insignificant because the respective control time losses are only very short.

The evaluation of the measurement of the internal resistance occurs in a particularly preferable way, i.e. the measurement of the altered Nernst voltage as a result of the superimposition of the test pulses, after the sample/hold. The control of the pump current source can thereby occur either continually on the basis of the signal for the Nernst voltage, also before the sample/hold, or digitally after conversion of the signal for the Nernst voltage, thus after the sample/hold. If the control of the pump current source occurs on the basis of a discretely converted signal, the same sample and hold circuit is advantageously used for said control as for the acquisition of the temperature.

The method according to the invention allows for measured values for $O_2$ as well as measured values for the internal resistance and thereby for a temperature measurement to be provided solely by acquisition of the Nernst voltage and in particular by digitization of the corresponding values and their digital processing. In a particularly preferred way, a scanning of the applicable measured values with at least two time constants, respectively corresponding filters, is performed. A first time constant is used for a quick scanning of the Nernst voltage for acquiring the internal resistance values as a reaction of the system to the discrete bipolar test pulses being applied. An additional time constant is provided for a slow scanning for the measured value generation during the closed-loop pump current control for measuring $O_2$. Because the same physical variable is evaluated here via various measuring channels, this method is also advantageous for diagnostic purposes.

In a particularly preferred configuration of the method according to the invention, the application of the bipolar test pulses is thereby used to apply a predeterminable effective probe direct current into the probe, in particular into the Nernst cell, by means of an appropriate design of pulse and counter pulse. In other words, a probe direct current resulting from pulse and counter pulse is controlled in the Nernst cell in a defined manner. In the case of a symmetrical definition of pulse and counter pulse, pulse and counter pulse cancel each other out so that no direct current flows as a result. For example, a decrease in length of the counter pulse results in a positive, respectively effective, current. This current can, for example, be controlled in defined form as reference pump current and, for example, be advantageously used with exhaust gas probes having a pumped reference. By means of an appropriate design of pulse and counter pulse, a current can, for example, be set in the range of between 0 µA to approximately 100 µA, in particular between approximately 0 µA to approximately 50 µA. This can, for example, be implemented by means of the length of the counter pulse at a frequency of the bipolar test pulses of 100 Hz at a pulse duration of 0.5 ms to 1 ms and at a pulse height of 0.5 mA to 1 mA.

The invention additionally comprises a device, which is designed in such a way that it is suitable for carrying out a method in the manner described above. In particular this device comprises a lambda probe, which can be heated via at least one heating element. Furthermore, the device is equipped with a circuit arrangement, which allows for a superimposition of discrete bipolar test pulses consisting of a pulse and a counter pulse and an acquisition of the Nernst voltage $U_N$ for measuring the internal resistance $R_i$ as a measurement for the temperature of the probe. With regard to additional characteristics of this device, reference will be made to the above description.

The invention further comprises a computer program, which executes all of the steps of the method described, if it is run on a computer, in particular in a control unit of an internal combustion engine. Finally the invention comprises a computer program product with a program code, which is stored on a machine-readable carrier, for carrying out the method according to the invention if the program is executed on a computer or in a control unit. This computer program, respectively the computer program product, is suited in a particularly advantageous manner to allow for a temperature measurement of an exhaust gas probe via a measurement of the internal resistance $R_i$ without significantly influencing the use of the Nernst voltage for the closed-loop control of the pump current as a measurement for the composition of the exhaust gas.

Additional advantages and characteristics of the invention become apparent in the following description of the figures in connection with the sub-claims and the description of examples of embodiment.

DETAILED DESCRIPTION

Figure 1:
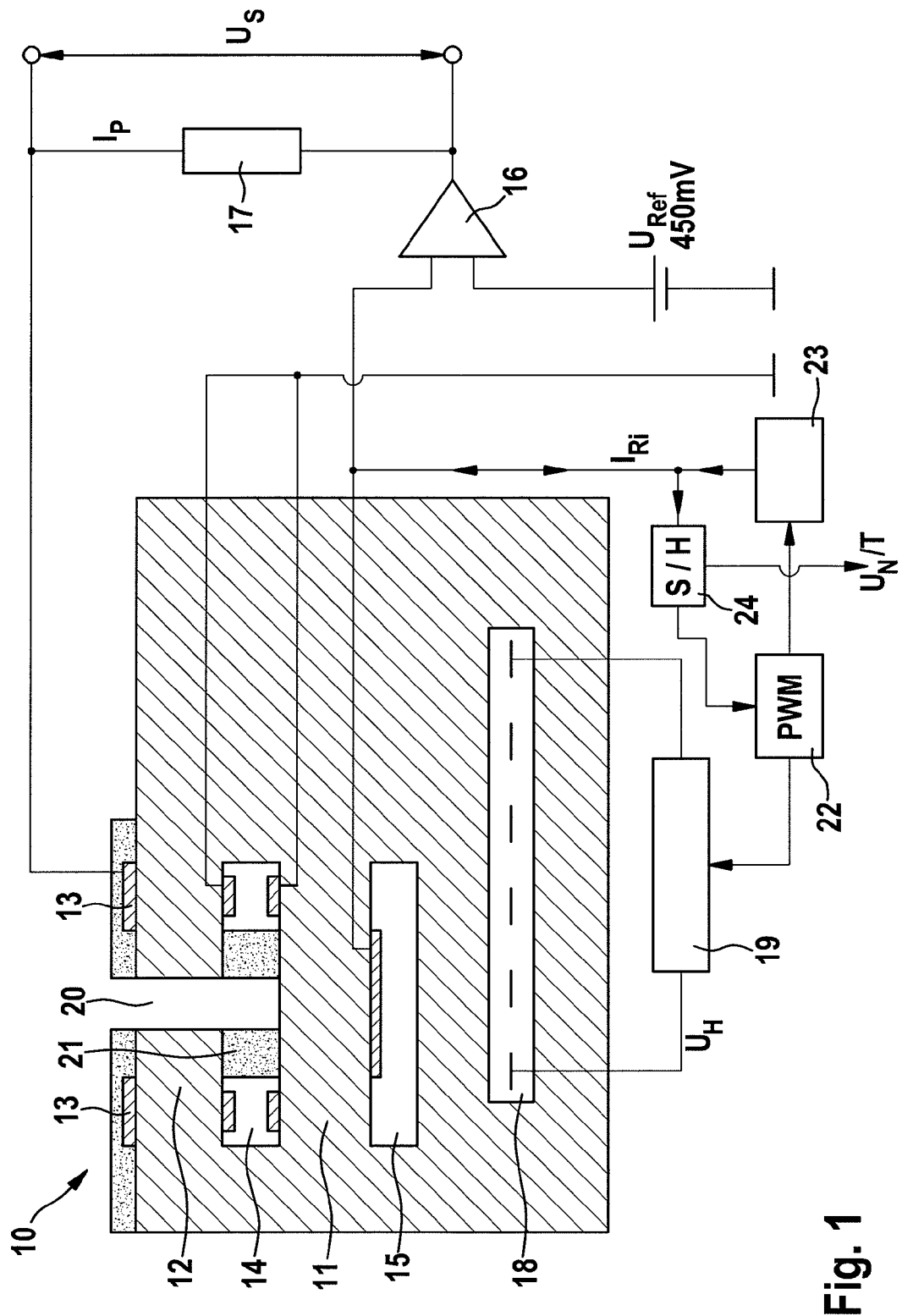
FIG. 1 shows a broadband lambda probe known from the technical field with a circuit arrangement for carrying out the method according to the invention.

In FIG. 1 a broadband lambda probe 10 from the technical field is depicted. The lambda probe is provided for measuring the residual oxygen content in the exhaust gas in order to be able to adjust the air/fuel mixture for the combustion in the internal combustion engine to a value of Lambda=1, i.e. for a stoichiometric ratio of air to fuel. The ceramic material used in the probe 10 has an electrical conductivity at high temperatures so that a galvanic voltage arises at the connections of the probe, which is characteristic for the oxygen content. The broadband lambda probe 10 which can be used for a wide lean range essentially consists of a combination of a concentration cell acting as a galvanic cell, respectively Nernst cell 11, and a limiting-current cell, respectively oxygen pump cell 12. The Nernst cell 11 is in a hollow cavity 14 with the measuring gas, which, for example, is configured in the form of a ring and is in connection with the exhaust gas via a diffusion canal 20 and a diffusion barrier 21. Said hollow cavity 14 is also in contact with a reference gas in a reference air channel 15. Besides being influenced by the exhaust gas, the measuring gas in the hollow cavity 14 is also influenced by a pump current, which is induced in the oxygen pump cell 12 and pumps the oxygen in or out of the hollow cavity 14. For this purpose, a voltage is applied to the pump cell 12 from outside via the outer pump electrode 13. The so-called pump current which emerges depends on the difference of the oxygen concentration on both sides of the probe and the adjusted voltage. Oxygen molecules are transported by the pump current. The pump current is adjusted by a comparator, respectively a closed-loop control circuit 16, in such a way that the oxygen flow by means of the electrical current of the pump cell 12 exactly equalizes the oxygen flow by means of the diffusion canal 20 so that the condition of Lambda=1 prevails in the measuring gas chamber 14. The respective pump current $I_P$ forms the output signal of the lambda probe 10 and can be tapped across a resistor 17 as pump or probe voltage $U_S$.

The lambda probe 10 additionally comprises a heater, respectively at least one heating element 18 for heating the probe. The heater 18 is activated via a heater output stage 19 and is impressed with the heating voltage $U_H$. The activation of the heater output stage 19 preferably occurs in a controlled manner via a pulse width modulation (PWM) 22.

The determination of the temperature is performed by measuring the internal resistance $R_i$ of the exhaust gas probe. For this purpose, discrete bipolar test pulses $I_{Ri}$ consisting of a pulse and a counter pulse are superimposed on the Nernst cell 11 according to the invention by a pulse/counter pulse generation 23, respectively a pulse generator; and the change in voltage, in particular the altered Nernst voltage $U_N$, as a reaction to said superimposition is acquired. Because the internal resistance $R_i$ is extremely temperature dependent, the temperature of the exhaust gas probe 10 can be suggested from the measured change in voltage. The acquisition of the changes in voltage induced by the applied test pulses preferably occurs by tapping the change in the Nernst voltage at a sample and hold circuit (S/H) 24. The value acquired for the temperature of the exhaust gas probe via the measurement for internal resistance preferably enters as an input signal into the control system of the heating element 18 via the pulse width modulation 22.

According to the invention, the test pulses are applied as pulse and counter pulse in opposite polarity. In so doing, a polarization of the exhaust gas probe is to a great extent avoided. The polarization of the probe arising in conventional pulsed internal resistance measuring methods has the following disadvantage: After being subjected each time to the test pulses, especially aged probes and those which have cooled down require a relatively long recovery phase for degrading the induced polarization before the Nernst voltage can again be acquired trouble-free. This disadvantage is corrected in the method according to the invention because a polarization of the probe by the test pulses is by and large avoided.

The point in time of the generation of the test pulses via the pulse generator 23, thus consisting of a pulse and a counter pulse, as well as the evaluation of the measurement for internal resistance via the sample and hold circuit (S/H) 24 is very advantageously generated from the PWM signal for the closed-loop control of the heater, respectively synchronized with the PWM control system.

Figure 2:
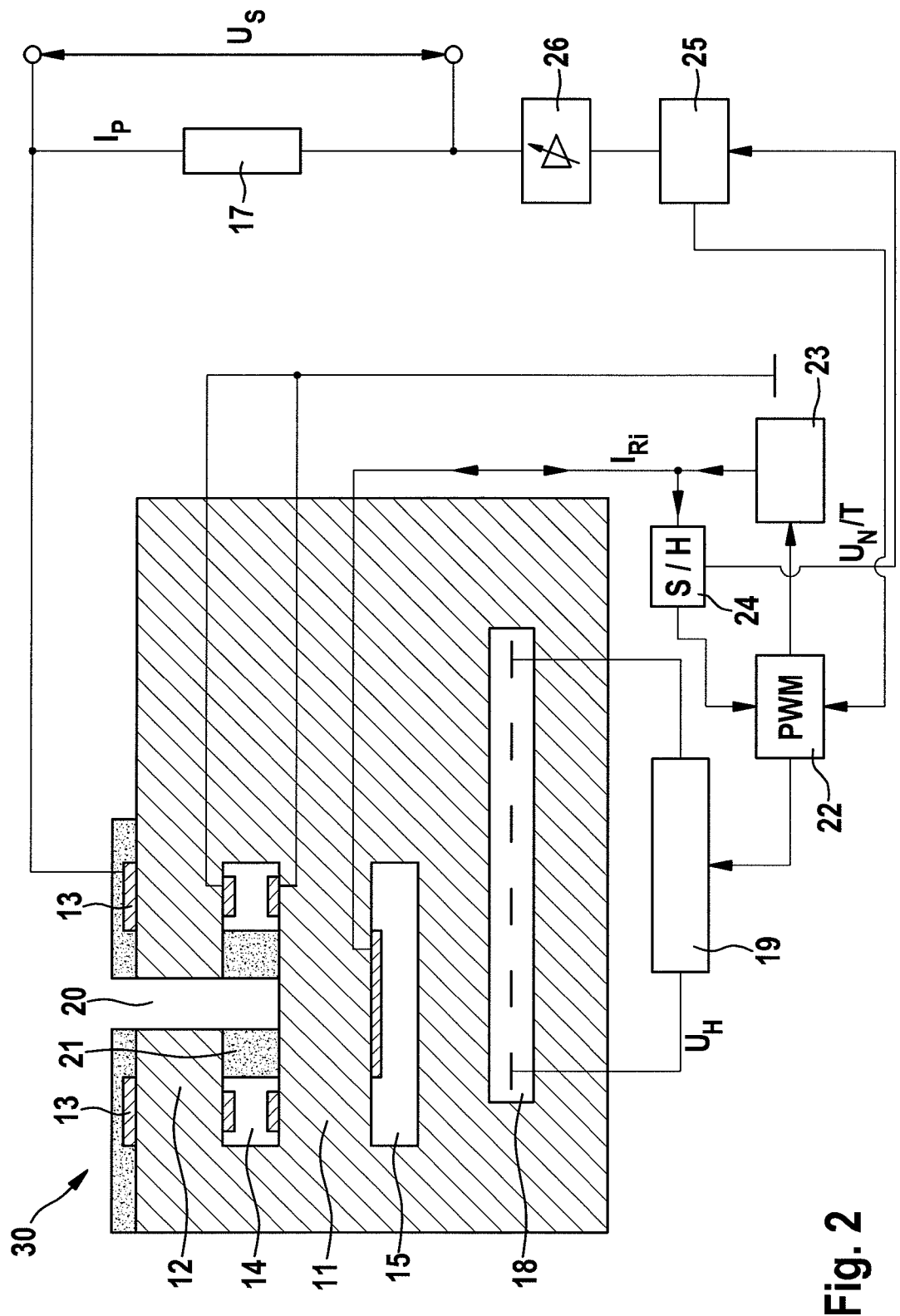
FIG. 2 shows a broadband lambda probe with an additional circuit arrangement for carrying out the method according to the invention.

FIG. 2 shows a broadband lambda probe 30 with an additional circuit arrangement for carrying out a preferred form of embodiment of the method according to the invention. Different elements of the broadband lambda probe in this form of embodiment correspond to the elements of the lambda probe 10 shown in FIG. 1 and are denoted with the same reference numerals. In contrast to the form of embodiment shown in FIG. 1, the Nernst voltage, which is acquired via the sample and hold circuit 24, is used to ascertain the internal resistance $R_i$ as a measurement for the temperature and as an input signal for the pump current closed-loop control in this form of embodiment according to the invention. For this purpose, the Nernst voltage $U_N$ acquired by means of the sample and hold circuit, is supplied as an input signal into a digital closed-loop control algorithm 25. The required pump current is ascertained in the digital closed-loop control algorithm 25 and is adjusted by a controllable current source, respectively voltage source 26, in such a way that the oxygen flow through the pump cell 12 exactly equalizes the oxygen flow through the diffusion channel 20, so that the condition Lambda=1 prevails in the measuring gas chamber 14. The pulse width modulation 22 with signals is also preferably activated from the digital closed-loop control algorithm.

In other forms of embodiment, the value for the Nernst voltage as a measurement for the temperature, which is ascertained via the sample and hold circuit 24, is immediately used as an input signal for the pulse width modulation.

Figure 3:
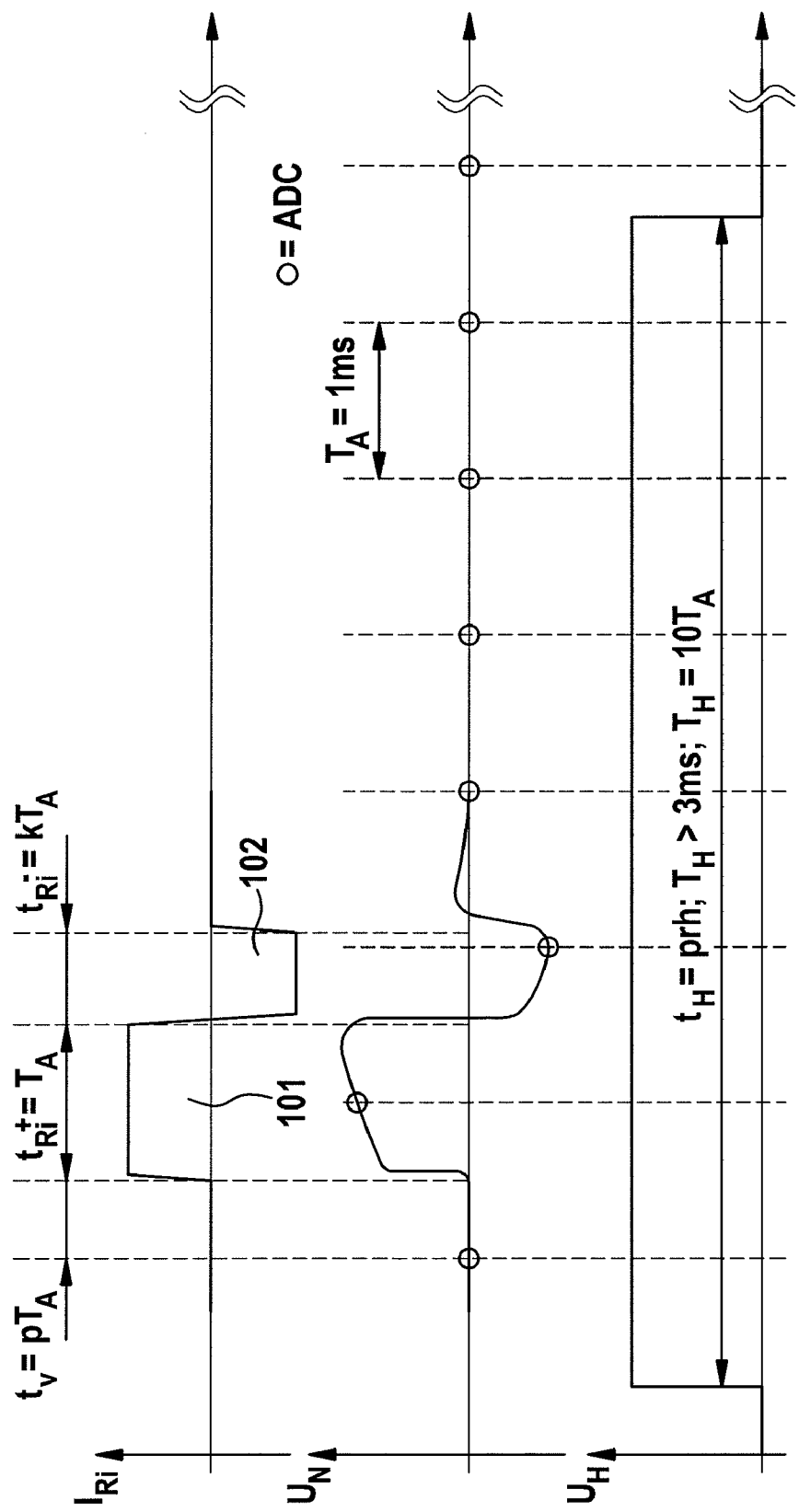
FIG. 3 shows a schematic depiction of the sequence of the method according to the invention by means of the temporal progression of the heater voltage, the test pulses and the Nernst voltage.

The temporal progressions of the heating voltage $U_H$, the Nernst voltage $U_N$ and the test pulses $I_{Ri}$ shown in FIG. 3 illustrate the implementation of the method according to the invention during a synchronization of the bipolar test pulses with the clock frequency of the activation of the heating element of a broadband probe. $U_H$ reflects the voltage applied at the heating element, said voltage being emitted as a pulse width modulation (PWM) to the heater's output stage. The heat output is adjusted via the switch-on time $t_H$. The required switch-on time is determined from a digital closed-loop control algorithm via the amplification prh:

$$t_H = prh$$

The pulse width in this instance is implemented with a frequency of 100 Hz. The Nernst voltage $U_N$ as a measurement for $O_2$, respectively for the air ratio lambda, is evaluated with a frequency of 1 ms. The circles reflect the evaluation times in intervals of $T_A = 1$ ms. The analog measured values are converted into digital values (ADC) for every evaluation and are further processed. The Nernst voltage $U_N$ is the input signal for a digitally implemented closed-loop control algorithm of the pump current of a broadband probe. The discrete bipolar test pulses consisting of a pulse 101 and a counter pulse 102 are completely implemented during the switch-on phase of the heating element and are superimposed on the Nernst cell.

The clock for the heating frequency $T_H$ is a multiple, in particular the decuple, of the clock for the evaluation of the Nernst voltage:

$$T_H = 10\, T_A$$

In the case of a lengthy switch-on time of the heater, in particular when a threshold of 7 ms is exceeded, a bipolar test pulse $I_{Ri}$ for measuring the internal resistance $R_i$ is started when switching on the heater. If the switch-on time undershoots 3 ms, a bipolar test pulse is started when switching off the heater.

Because the scanning of the Nernst voltage and the activation of the heater are not synchronized, the position of the bipolar test pulse can shift by $t_v = pT_A < 1$ ms. Because the heater flank following the bipolar test pulse occurs at the earliest after 3 ms, the bipolar test pulse reliably lies outside of the heater flank after the first ADC conversion of the Nernst voltage. The innovative method thus avoids that a heater flank occurs during the test pulses and disturbs the $R_i$ measurement.

The first pulse 101 of the bipolar test pulse is applied as a positive flank for a time duration of 1 ms, which corresponds to the evaluation clock $T_A$:

$$t_{Ri}^+ = T_A$$

The time duration of the negative flank as a counter pulse 102 of the bipolar test pulse is shortened by a constant factor k:

$$t_{Ri}^- = kT_A$$

The acquired Nernst voltage $U_N$ reflects in a slightly time-lagged fashion the temperature dependant change in voltage as a reaction of the system to the applied test pulse $I_{Ri}$ and can be used as a measured variable for the temperature measurement.

On account of the shortening of the counter pulse, an effective probe direct current occurs in the Nernst cell as a result. This probe direct current can be controlled, for example, via a reference pump current via the factor k. In the case of the design, which was selected by way of example, of the frequency of the test pulses of 100 Hz and of a pulse duration of 0.5 to 1 ms at a pulse height of 0.5 mA to 1 mA, the resulting probe direct current can be adjusted in a range of approximately 0 µA to approximately 50 µA.

The synchronization with the applied heating voltage $U_H$ preferably occurs via the logic level, which activates the heater output stage. A synchronization via the voltage level at the heater element is likewise possible.

The invention claimed is:

1. A method for operating an exhaust gas probe in an exhaust gas of an internal combustion engine, wherein the exhaust gas probe comprises at least one heating element for achieving an operating temperature of the exhaust gas probe and a determination of the temperature occurs by measuring the internal resistance of the exhaust gas probe, the method comprising:
measuring the internal resistance by superimposing discrete bipolar direct current test pulses comprising a first discrete level pulse with a first polarity followed by a second discrete level pulse with an opposite polarity and by acquiring a Nernst voltage.

2. The method of claim 1, further comprising activating the heating element in a clocked manner and synchronizing the bipolar test pulses with a clock frequency of the activation of the heating element.

3. The method of claim 1, further comprising applying the bipolar test pulses during at least one of a switch-on phase and a switch-off phase of the heating element.

4. The method of claim 1, further comprising implementing at least one of a pump current closed-loop control and a closed-loop control of the heating element via a digital closed-loop control algorithm.

5. The method of claim 1, further comprising bipolar test pulses of approximately 0.1 ms to approximately 5 ms.

6. The method of claim 5, wherein the bipolar test pulses are approximately 0.5 ms to approximately 1 ms.

7. The method of claim 1, further comprising applying an effective probe direct current by an asymmetric superimposition of the pulse and the counter pulse, wherein the effective probe direct current lies in a range between 0 and approximately 100 µA.

8. The method of claim 7, wherein the effective probe direct current lies in a range between 0 and approximately 50 µA.

9. The method of claim 1, further comprising acquiring the Nernst voltage as an input signal for a pump current closed-loop control of the exhaust gas probe, wherein a sample and hold circuit acquires the Nernst voltage for measuring the internal resistance.

10. The method of claim 9, further comprising suspending acquisition of the Nernst voltage as an input signal for the pump current closed-loop control of the exhaust gas probe during measurement of the internal resistance.

11. The method of claim 10, further comprising performing a mathematical compensation for a time period of the suspension of the use of the Nernst voltage as an input signal for the pump current closed-loop control.

12. A device configured to operate an exhaust gas probe in an exhaust gas of an internal combustion engine, wherein the exhaust gas probe comprises:
at least one heating element for achieving an operating temperature of the exhaust gas probe;

wherein a determination of the temperature occurs by measuring the internal resistance of the exhaust gas probe by superimposing discrete bipolar direct current test pulses comprising a first discrete level pulse with a first polarity followed by a second discrete level pulse with an opposite polarity and by acquiring a Nernst voltage.

13. A computer program in a control unit of an internal combustion engine configured to operate an exhaust gas probe in an exhaust gas of an internal combustion engine, wherein the exhaust gas probe comprises:
   at least one heating element for achieving an operating temperature of the exhaust gas probe;
   wherein a determination of the temperature occurs by measuring the internal resistance of the exhaust gas probe by superimposing discrete bipolar direct current test pulses comprising a first discrete level pulse with a first polarity followed by a second discrete level pulse with an opposite polarity and by acquiring a Nernst voltage.

14. A computer program product with a program code, that is stored on a machine-readable carrier configured to operate an exhaust gas probe in an exhaust gas of an internal combustion engine, wherein the exhaust gas probe comprises:
   at least one heating element for achieving an operating temperature of the exhaust gas probe;
   wherein a determination of the temperature occurs by measuring the internal resistance of the exhaust gas probe by superimposing discrete bipolar direct current test pulses comprising a first discrete level pulse with a first polarity followed by a second discrete level pulse with an opposite polarity and by acquiring a Nernst voltage.

* * * * *